United States Patent
Maschke

(10) Patent No.: US 7,496,399 B2
(45) Date of Patent: Feb. 24, 2009

(54) METHOD AND DEVICE FOR EXAMINING THE SKIN

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 756 days.

(21) Appl. No.: 11/037,324

(22) Filed: Jan. 18, 2005

(65) Prior Publication Data

US 2005/0171439 A1 Aug. 4, 2005

(30) Foreign Application Priority Data

Jan. 20, 2004 (DE) .................... 10 2004 002 918

(51) Int. Cl.
*A61B 5/00* (2006.01)
(52) U.S. Cl. .................... 600/476; 600/425; 600/473
(58) Field of Classification Search ................ 600/476, 600/425, 407, 300, 473, 306; 382/128; 356/479, 356/244, 369
See application file for complete search history.

(56) References Cited

U.S. PATENT DOCUMENTS 6,081,612 A * 6/2000 Gutkowicz-Krusin et al. .... 382/128

FOREIGN PATENT DOCUMENTS

DE 197 54 909 C2 6/1999
EP 0 815 801 B1 1/1998

OTHER PUBLICATIONS

"Alarmzeichen der Haut—jetzt rasch zum Facharzt", MMW-Fortschritte der Medizin, Nr. Jun. 2003, p. 36, Germany.
Richard J. Antcliff, Timothy J. Ffytche, John S. Shilling, John Marshall, "Optical Coherence Tomography of Melanocytoma", American Journal of Ophthalmology, Dec. 2000, pp. 845-847, vol. 130, No. 6, USA.
Francisco Macedo Paschoal, "Early Diagnosis of Melanoma by Surface Microscopy (Dermatoscopy)", São Paulo Medical Journal/RPM 114(4), 1996, pp. 1220-1221, Brazil.

* cited by examiner

*Primary Examiner*—Eric F Winakur
*Assistant Examiner*—Lawrence N Laryea

(57) ABSTRACT

For an improved method for examining the skin of a proband, in particular as part of a skin cancer screening examination or a skin cancer therapy, it is provided that an epiluminescence microscopy image (B) is first taken of a distinctive skin site and by analysis of the image (B) the skin site is rated as suspect or inconsequential with regard to the presence of a disease. In a further method step it is provided that an image (B') of a skin site rated as suspect is recorded by means of optical coherence tomography and the diagnosis of disease is verified or refuted on the basis of this image (B'). A device particularly suited to the performance of the method comprises an epiluminescence microscopy device (2) and an optical coherence tomography device (3) together with a common control unit (6).

10 Claims, 2 Drawing Sheets

METHOD AND DEVICE FOR EXAMINING THE SKIN

CROSS REFERENCE TO RELATED APPLICATIONS

This application claims priority to the German application No. 10 2004 002 918.0, filed Jan. 20, 2004 which is incorporated by reference herein in its entirety.

FIELD OF INVENTION

The invention relates to a method for examining the skin of a proband, in particular as part of a skin cancer screening examination or a skin cancer therapy. The invention further relates to a device for performing the method.

BACKGROUND OF INVENTION

It has been possible to observe a significant increase in the incidence of skin cancer diseases in recent times. The principal cause of this is the increasing trend for people to expose themselves to intensive solar radiation. The most common skin disease having fatal consequences is that which is known as malignant melanoma, which occurs in the Central European region, for example, with an incidence of approximately $12/100,000$ of the population/year (Fortschritte der Medizin (title of German medical journal meaning "Advances in Medicine"), No. 6, 2003).

Provided the skin disease is diagnosed at a sufficiently early stage and therapy, which generally involves surgical removal of the diseased tissue, is initiated immediately, the prospects of recovery are good. However, early detection of the disease poses problems.

Until now, an examination of the skin for skin cancer has mostly involved a visual examination performed with the aid of a magnifying lens. In the course of this examination the dermatologist analyzes abnormalities of the skin such as, for example, pigmented moles or skin lesions (nevi). These are usually checked for asymmetry, border irregularity, color variability and diameter. An irregularly and indistinctly bordered skin abnormality with mixed pigmentation and anametically observed growth tendency is highly suspect with regard to malignancy.

SUMMARY OF INVENTION

An examination method having greater selectivity, that is to say providing enhanced diagnostic authority, is epiluminescence microscopy. An epiluminescence microscope allows in particular an examination of the dermis, i.e. the sub-surface layer of the skin, which is especially important for a diagnosis of skin cancer. However, conventional epiluminescence microscopes are only suitable to a limited extent for a fast and efficient examination for skin cancer. For example, the use of a conventional epiluminescence microscope frequently requires an immersion oil to be applied between the skin being examined and the lens of the epiluminescence microscope. However, this technique is problematical particularly in clinical use, especially as it is virtually impossible to avoid entrapping air in the immersion oil. Air bubbles caused in this way can make the diagnosis more difficult and lead in particular to a distortion of the results of the analysis.

Although digital epiluminescence microscopes (incident light microscopes) equipped with polarization filters and used without immersion oil are known for example from EP 0 794 731 A1, when an epiluminescence microscope of this kind is used for a relatively long time there is frequently thermal stress on the skin tissue caused as a result of the incident light sources used. Moreover, a digital epiluminescence microscope typically has only a comparatively low local resolution, particularly in deeper lying layers of the dermis. However, it is precisely a good local resolution of deeper lying skin layers that is of great importance for the diagnosis of skin cancer and the preparation for a surgical intervention.

A comparatively new technique which has a good local resolution of deeper lying skin layers is what is known optical coherence tomography (OCT). The way in which OCT operates is analogous to an image-generating ultrasound examination method (B-scan mode), as is commonly employed particularly in the medical domain. With OCT, however, light waves rather than ultrasound waves are used. The analyzer of an OCT device operates on the basic principle of a Michelson interferometer. Methods based on OCT are described for example in U.S. Pat. No. 5,921,926. A disadvantage of OCT resides in the greatly reduced viewing field of this technology. For this reason OCT is not suitable for examining a relatively large area of skin.

Furthermore, a surgical microscope with integrated OCT device is known from EP 0 815 801 B1.

An object of the present invention is to specify an improved method for examining the skin. A further object of the invention is to specify a device that is particularly suitable for performing the method.

These objects are achieved by the claims.

According to said method, in a first method step a digital image of a distinctive point on the skin (hereinafter referred to as a "skin site") is recorded using epiluminescence microscopy and analyzed by electronic means for indications of the presence of a disease, in particular skin cancer. Depending on the results of said analysis, the skin site is then rated as suspect, i.e. potentially diseased (malignant), or as inconsequential (benign). In the case of a skin site rated as suspect, a recording is taken using optical coherence tomography. The term "recording" firstly includes a data record containing a diffraction pattern, whereby the diffraction pattern is generated by interference overlaying, with a reference light beam, of a coherence light beam scattered back by the skin tissue. The term "recording" further includes an image of the recorded skin site, which image is produced from the diffraction pattern by means of mathematical methods common in the context of OCT.

By means of the method according to the invention the techniques of epiluminescence microscopy and OCT, which are known per se, are combined with one another in such a way that the advantages of the respective examination method are exploited, whereas their disadvantages are canceled out. As epiluminescence microscopy features a comparatively large image cross-section, when it is used as a kind of preliminary examination a relatively large area of the skin can also be examined in a satisfactorily short time. The comparatively low local resolution of epiluminescence microscopy is not a disadvantage here, especially as an excellent local resolution of up to 10 μm at a penetration depth of 1 to 3 mm into the skin being examined is guaranteed by the following method step of OCT in the case of a suspect skin lesion. In the method according to the invention the thermal stress imposed on the skin as a result of the epiluminescence microscope examination is reduced to an acceptable level, especially since with epiluminescence microscopy the skin is only "scanned" comparatively quickly and so the individual skin site is exposed only briefly to the incident light.

In order to effectively prevent errors due to carelessness or similar, the method is automated with regard to the pre-classification of the examined skin sites. It is provided for this purpose in particular that the epiluminescence microscopy image is taken in digital form and analyzed using electronic image processing means according to at least one predefined selection rule for indications for the presence of disease. Such selection rules include in particular the examination of the size, shape and pigmentation, i.e. skin coloration, of a suspect skin site and its assessment on the basis of predefined threshold values. Suspect skin sites are therefore detected and indicated automatically.

According to said device, the device includes an integrated epiluminescence microscopy device and an optical coherence tomography device. Both said devices have recourse in this case to a common control unit.

The integrated device produces a substantial simplification in terms of handling for the examining physician. The reason for this is firstly that the handling of the two examination methods is standardized as a result of the common control unit. Secondly, the common control unit offers in a straightforward way a simple means of merging the data generated by both examination methods for collective analysis or archiving, of overlaying said data or of using it synergetically in some other way. Furthermore, the integration of epiluminescence microscopy and OCT in a common device provides a substantial cost benefit compared with two individual devices.

The device is provided with a first handle applicator as part of the epiluminescence microscopy device, which applicator is equipped with a microscopic lens, at least one incident light source and means for transmitting an epiluminescence microscopy image to an image processing unit. In terms of its external form the handle applicator is embodied in particular in the shape of a pen or pistol in order to enable the examining physician to handle it easily. The means for transmitting the epiluminescence microscopy image preferably comprise a digital image detector disposed in the handle applicator, e.g. a CCD camera and an electronic data line via which the image data is transmitted electronically from the image detector to the image processing unit. In this arrangement the image processing unit is used for editing the image data with regard to contrast, sharpness etc. as well as, where applicable, for converting the image data into an easily manageable data format.

Alternatively, however, the images generated in the handle applicator can also be transmitted to the image processing unit in analog form, e.g. by means of a fiber optic cable. In this case the conversion of the analog images into digital image data takes place in the image processing unit.

The coherence tomography device comprises a second handle applicator, the application end of which is connected to a generator/analyzer unit by means of an optical waveguide, e.g. a fiber optic cable. The generator/analyzer unit comprises a light source for coherence light, in particular a laser, and an interferometer which is embodied in particular in the manner of a Michelson interferometer.

The control unit usefully comprises an image evaluation module which is embodied for the quantitative evaluation of image data, in particular for pattern recognition as well as for geometric and color analysis of the image or of individual patterns. Advantageously the epiluminescence microscopy image and if necessary also the coherence tomography image can be analyzed using the image evaluation module.

BRIEF DESCRIPTION OF THE DRAWINGS

An exemplary embodiment of the invention will be explained in more detail below with reference to a drawing, in which.

Parts and quantities corresponding to one another are provided with the same reference numerals in all the figures.

DETAILED DESCRIPTION OF INVENTION

Figure 1:
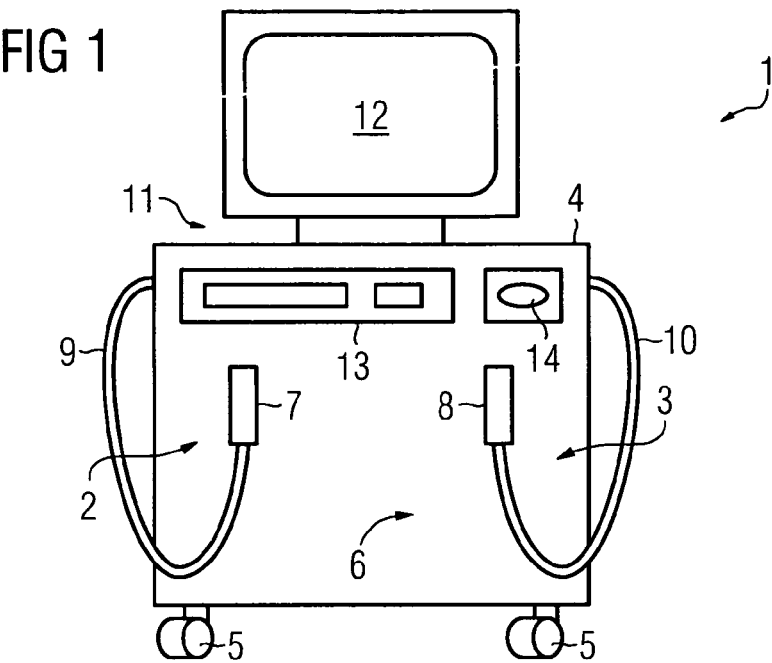
FIG. 1 shows a schematic plan view of a device for examining the skin of a proband, comprising an epiluminescence microscopy device and an optical coherence tomography device.

The device 1 shown in FIG. 1 comprises an epiluminescence microscopy device 2 and an optical coherence tomography device, abbreviated below to OCT device 3, which are integrated in a common housing 4. The housing 4 is preferably mounted on rollers 5 so as to be mobile and movable. It further comprises a control unit 6 (hidden in the housing 4 in the illustration according to FIG. 1) that is common to both devices 2 and 3 and that in particular comprises a data processing system. The epiluminescence microscopy device 2 and the OCT device 3 are each equipped with a handle applicator 7 and 8 respectively.

Figure 2:
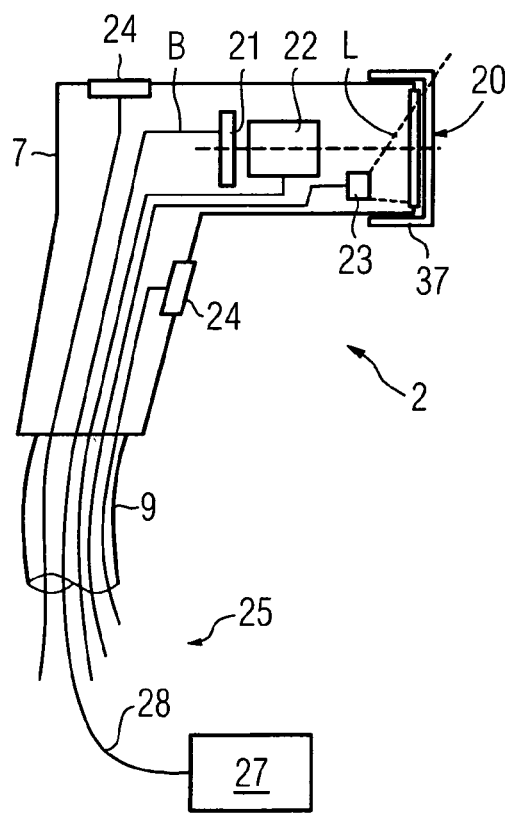
FIG. 2 shows a schematic representation of a handle applicator of the epiluminescence microscopy device according to FIG. 1.
Figure 3:
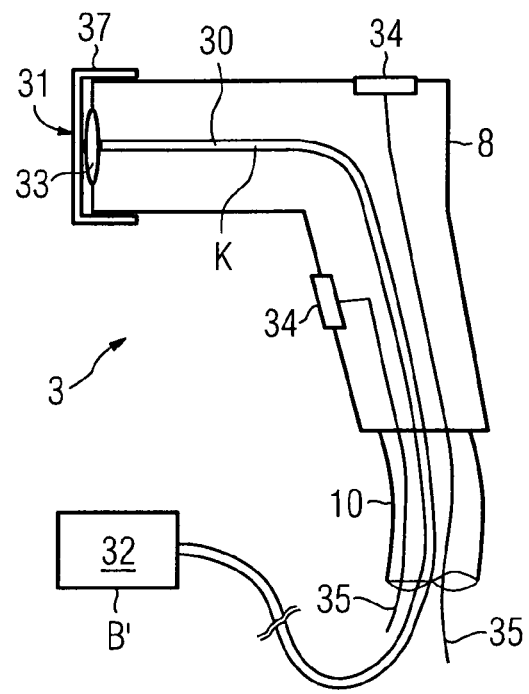
FIG. 3 shows, in a representation according to FIG. 2, a handle applicator of the coherence tomography device as shown in FIG. 1.

Each handle applicator 7,8 is—as can be clearly seen from FIGS. 2 and 3—embodied in the form of a pistol so as to be easy to handle for an examining physician and is connected to the housing 4 in each case by means of an associated supply tube 9 and 10 respectively.

The housing 4 also carries input/output means 11 for operating the control unit 6. Said input/output means 11 comprise in particular a monitor 12, a keyboard 13 and a non-alphanumeric input device 14 such as e.g. a trackball, a mouse, a joystick or similar.

Figure 4:
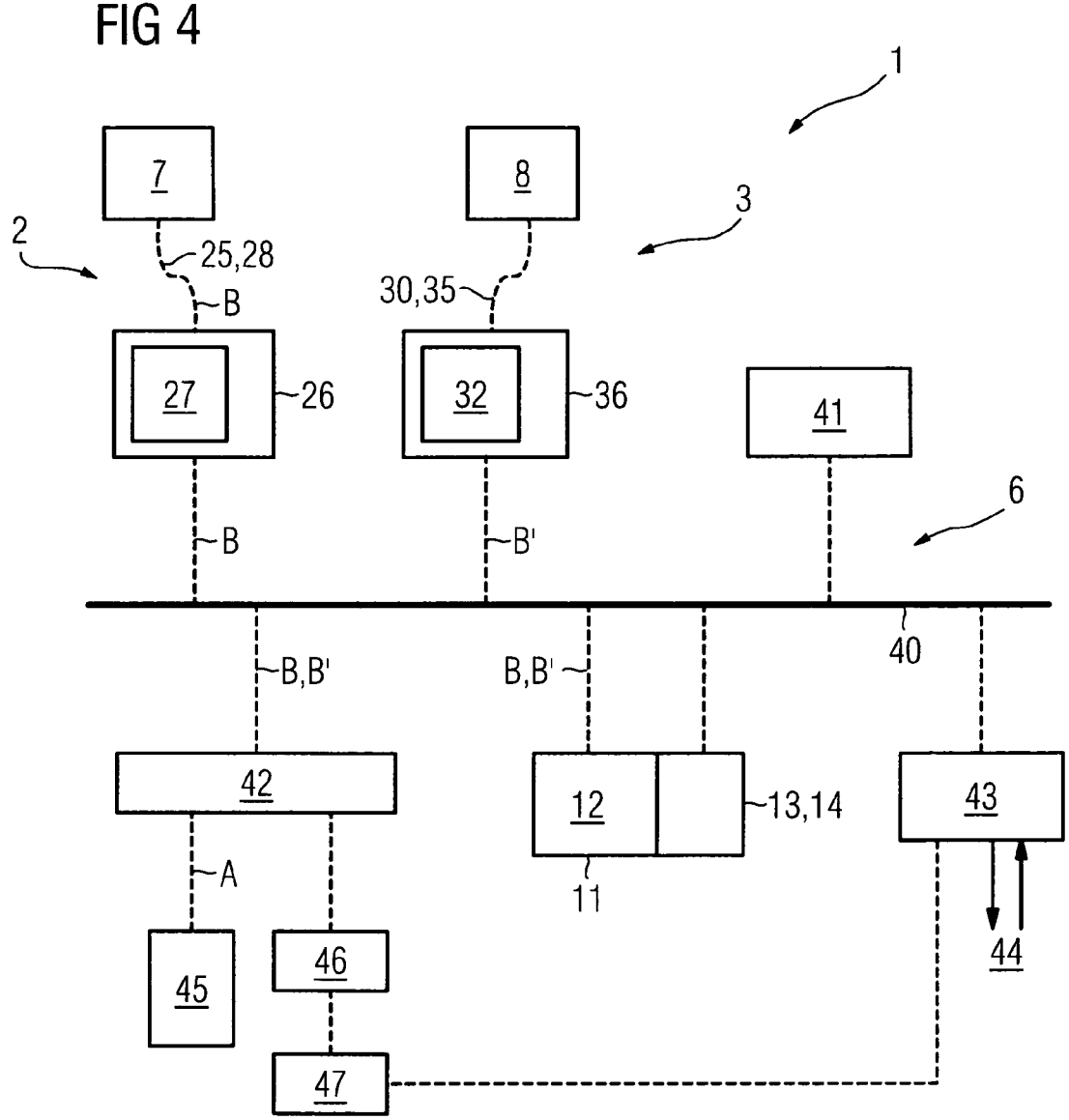
FIG. 4 is a schematic circuit diagram of the device according to FIG. 1.

The handle applicator 7 of the epiluminescence microscopy device 2 shown in a schematic cross-sectional view in FIG. 2 contains a digital image detector 21 oriented toward one application end 20 with a microscopic lens 22 connected upstream thereof. The handle applicator 7 further contains at least one light source 23, embodied as a halogen lamp for illuminating an area located upstream of the application end 20 with incident light L. The handle applicator 7 also carries a number of control elements 24, in particular in the form of keys or similar, by means of which e.g. the recording of an epiluminescence microscopy image B can be initiated. The image detector 21, the lens 22, the light source 23 and the control elements 24 are connected via signal lines 25 which are routed, protected in the interior of the supply tube 9, to the housing 4 for the purpose of control by means of an interface module 26 (FIG. 4). The interface module 26 contains an image processing unit 27 for editing the image(s) B. To permit digital transmission of the epiluminescence microscopy image B, the image detector 21 is connected to the image processing unit 27 via an image data line 28.

The handle applicator 8 of the OCT device 3 shown in FIG. 3 contains an optical waveguide 30, in particular a fiber optic cable, which connects the application end 31 of the handle applicator 8 to a generator/analyzer unit 32 (disposed inside the housing 4). The application end 31 is provided with an exit lens 33 so that, for the purpose of generating a coherence tomography image B', coherence light K generated by the generator/analyzer unit 32 can be emitted via the optical waveguide 30 through the application end 31 of the handle applicator 8 and back-scattered coherence light K can be intercepted by the application end 31 and delivered to the generator/analyzer unit 32 for analysis. The generator/analyzer unit 32 contains a light source (not shown in any greater detail), in particular a laser, for generating the coherence light K and an interferometer for analyzing the back-scattered coherence light K.

The handle applicator 8, analogously to the handle applicator 7, further comprises control elements 34 for controlling the method. The control elements 34 are connected via signal lines 35 which are routed in the supply tube 10 to an interface module 36 disposed in the housing 4, which interface module contains the generator/analyzer unit 32.

For reasons of hygiene both handle applicators 7 and 8 are each provided with a replaceable transparent cap 37 which is placed onto the respective application end 20 and 31.

The layout of the device 1 is shown in schematic form in FIG. 4 in a simplified functional diagram. It can be seen from the figure that the epiluminescence microscopy device 2 and the OCT device 3 are connected to a data bus 40 of the control unit 6. The epiluminescence microscopy device 2 and the coherence tomography device 3 are controlled by a system controller 41 via this data bus 40.

Also connected to the data bus 40 are an image evaluation unit 42 for analyzing the epiluminescence microscopy image B and the coherence tomography image B', together with the input/output means 11 comprising the monitor 12, the keyboard 13 and the input device 14. The control unit 6 further comprises an interface 43 for communicating with an external data network 44, in particular the Internet.

The image evaluation unit 42 operates in the context of electronic pattern recognition in accordance with a set of selection rules A which are specified for the image evaluation unit 42 from a rule memory 45. For the purpose of storing image data the image evaluation unit 42 is connected to an image and data memory 46 and a CD read/write device 47.

In advance of the performance of the method, distinctive skin sites of a proband are determined first by visual examination. A distinctive skin site of this kind can be, for example, a pigmented mole or similar. When a distinctive skin site is found, the examining physician places the handle applicator 7 of the epiluminescence microscopy device 2 with the application end 20 onto the distinctive skin site of the proband and triggers the recording of an epiluminescence microscopy image B by the image detector 21 by actuating the control elements 24. While the recording is being taken, the skin site is brightly illuminated by means of the light source 23.

The epiluminescence microscopy image B or where appropriate a series of such images is routed to the image processing unit 27 and edited therein with regard to focus and contrast. Where necessary, a plurality of individual images recorded using the handle applicator 7 can be assembled "like a puzzle" in the image processing unit 27 to form a complete image. The edited image B is supplied to the image evaluation unit 42, where it is subjected to a quantitative analysis. The image evaluation unit 42 is equipped with electronic pattern recognition means, with the aid of which it detects distinctive skin sites such as pigmented moles etc. The image evaluation unit 42 examines hereupon geometric and color properties of the suspect skin site and evaluates this information on the basis of predefined selection rules A with regard to a possible diagnosis of disease. Thus, for example, a skin lesion is rated as suspect if its diameter or asymmetry exceeds a predefined threshold value. A skin lesion can also be rated as suspect if its borderline is recognized as irregular or a mixed pigmentation is present. The image B is subsequently or simultaneously displayed on the monitor 12. In addition the image evaluation unit 42 outputs the result of the quantitative analysis. A warning message is output in particular if a suspect skin site is recognized in the image B.

The warning message provides support by drawing the attention of the examining physician to the possible presence of disease. It is now provided according to the method that OCT be used either to verify or refute a disease diagnosis of this kind. Toward that end the examining physician places the handle applicator 8 with its application end 31 onto the skin site rated as suspect and starts an OCT examination by actuating the control elements 34.

In the course of this examination, coherence light K, in particular laser light, is generated by the generator/analyzer unit 32 and beamed via the optical waveguide 30 and the exit lens 33 into the skin of the proband. The exit lens 33 collects back-scattered coherence light K and returns it via the optical waveguide 30 to the generator/analyzer unit 32. The back-scattered coherence light K is interferometrically analyzed in the generator/analyzer unit 32. In an analogous manner to an image-generating ultrasound method, it is possible by analysis of the coherence light K to generate an image (identified as image B' in the figure) of the dermis of the proband, said image having an excellent local resolution of approximately 10 μm down to a penetration depth of 1 to 3 mm into the skin tissue. The coherence tomography image B' is displayed in turn on the monitor 12 and quantitatively evaluated in the image evaluation unit 42. Based on the image B' and the result of the quantitative analysis the examining physician can decide with great confidence whether a distinctive skin site contains tumor-like tissue.

The data from the images B and B' is subsequently stored in the image data memory 46 or burned onto CD-ROM by means of the read/write device 47. The images B, B' can also be externally archived via the interface 43.

The invention claimed is:

1. A method for examining the skin of a patient, comprising:
   recording a digital epiluminescence microscopy image of an area of the skin;
   applying an evaluation rule to the digital epiluminescence microscopy image with an electronic image evaluation unit to classify the image as suspect or as inconsequential with regard to a presence of a skin disease, and to determine whether an optical coherence tomography measurement is required when the area of skin is evaluated as suspect with regard to the skin disease;
   recording a further image of the skin area using optical coherence tomography when required based upon the determining step.

2. A device for examining the skin of a patient, comprising:
   an epiluminescence microscope having a first handle, the first handle comprising a microscopic lens, a light source for generating incident light and transmission circuitry for transmitting an epiluminescence microscopy image to an image processing unit;
   an optical coherence tomography device having a second handle, the second handle comprising a light processing unit for emitting and capturing coherence light; and a common control unit that controls both the epiluminescence microscope and the optical coherence tomography device.

3. The device according to claim 2, wherein the control unit controls the epiluminescence microscope and the optical coherence tomography device such that the optical coherence tomography device is activated only in consequence of a preceding operation of the epiluminescence microscope and upon fulfillment of an activation criterion.

4. The device according to claim 2, wherein the transmission circuitry comprises a digital image detector and a data line for transmitting digital image data.

5. The device according to claim 2, wherein the transmission circuitry comprises an optical fiber arranged downstream of the lens for an analog transmission of the epiluminescence microscopy image.

6. The device according to claim 2, wherein the light processing unit comprises an optical fiber for optically connecting an end of the second handle to a generator/analyzer unit.

7. The device according to claim 2, wherein the control unit comprises an image evaluation unit which is adapted to perform a quantitative analysis of the epiluminescence microscopy image and a coherence tomography image recorded by the optical coherence tomography device.

8. The device of claim 2 wherein the control unit integrates functionality of the epiluminescence microscope and the optical coherence tomography device, with image data derived from each being storable in one memory device and displayable on the same monitor.

9. The device of claim 8 wherein the control unit includes an evaluation unit for evaluating both the epiluminescence microscopy image and an image generated from the optical coherence tomography device.

10. The device of claim 9 wherein the evaluation unit provides information enabling a person to determine, initially based on the epiluminescence microscopy image and then based on the optical coherence tomography, whether a distinctive skin site contains tumor-like tissue.

* * * * *